United States Patent
Morley et al.

(10) Patent No.: US 11,213,478 B2
(45) Date of Patent: Jan. 4, 2022

(54) COMPOSITIONS AND METHODS FOR HAIR REGROWTH

(71) Applicants: Myriam Morley, Westerly, RI (US); Sophia Kogan, New York, NY (US)

(72) Inventors: Myriam Morley, Westerly, RI (US); Sophia Kogan, New York, NY (US)

(73) Assignee: Nutraceutical Wellness Inc., New York, NY (US)

( * ) Notice: Subject to any disclaimer, the term of this patent is extended or adjusted under 35 U.S.C. 154(b) by 0 days.

(21) Appl. No.: 16/908,424

(22) Filed: Jun. 22, 2020

(65) Prior Publication Data

US 2020/0315949 A1    Oct. 8, 2020

Related U.S. Application Data

(63) Continuation of application No. 15/898,206, filed on Feb. 15, 2018, now Pat. No. 10,688,037, which is a continuation-in-part of application No. 14/986,525, filed on Dec. 31, 2015, now Pat. No. 10,709,659.

(51) Int. Cl.

| | |
|---|---|
| *A61P 17/14* | (2006.01) |
| *A61K 36/00* | (2006.01) |
| *A61K 8/9783* | (2017.01) |
| *A61K 8/73* | (2006.01) |
| *A61K 8/67* | (2006.01) |
| *A61K 8/65* | (2006.01) |
| *A61K 8/34* | (2006.01) |
| *A61K 8/20* | (2006.01) |
| *A61Q 7/00* | (2006.01) |
| *A23L 33/105* | (2016.01) |

(52) U.S. Cl.
CPC .......... *A61K 8/9783* (2017.08); *A23L 33/105* (2016.08); *A61K 8/20* (2013.01); *A61K 8/347* (2013.01); *A61K 8/65* (2013.01); *A61K 8/671* (2013.01); *A61K 8/673* (2013.01); *A61K 8/676* (2013.01); *A61K 8/678* (2013.01); *A61K 8/735* (2013.01); *A61Q 7/00* (2013.01); *A61P 17/14* (2018.01)

(58) Field of Classification Search
CPC ...................................................... A61P 17/14
See application file for complete search history.

(56) References Cited

U.S. PATENT DOCUMENTS

| | | |
|---|---|---|
| 10,688,037 B1 | 6/2020 | Morley et al. |
| 10,709,659 B1 | 7/2020 | Morley |

FOREIGN PATENT DOCUMENTS

| | | | | |
|---|---|---|---|---|
| ES | 2517741 | | 11/2014 | |
| GB | 2484812 | | 4/2012 | |
| GB | 2484812 A | * | 4/2012 | ............. A61K 36/15 |
| WO | WO 2015099842 | | 7/2015 | |

OTHER PUBLICATIONS

U.S. Appl. No. 16/927,708, filed Jul. 13, 2020, pp. 1-47.
Kalani et al., "Ashwagandha Root in the Treatment of Non-Classical Adrenal Hyperplasia", in Endocrine Reviews, vol. 33, No. 3, Jun. 2012, pp. 1-4.
Kalani, Amir; Bahtiyar, Gul; Sacerdote, Alan. "Ashwagandha root in the treatment of non-classical adrenal hyperplasia". BMJ case reports. 2012; 2012.
Notice of Allowance dated Feb. 11, 2020 in U.S. Appl. No. 15/898,206.
Notice of Allowance dated Mar. 10, 2020 in U.S. Appl. No. 14/986,525.
Nutrafol Men, available for sale Feb. 16, 2017, available from Internet, URL: https://nutrafol.com/products/.
Nutrafol Women, available for sale Feb. 16, 2017, available from Internet, URL: https://nutrafol.com/products/.
Office Action dated Mar. 5, 2018 in U.S. Appl. No. 14/986,525.
Office Action dated Jun. 19, 2019 in U.S. Appl. No. 14/986,525.
Office Action dated Oct. 7, 2019 in U.S. Appl. No. 15/898,206.
Office Action dated Nov. 22, 2019 in U.S. Appl. No. 14/986,525.
Restriction Requirement dated Feb. 26, 2019 in U.S. Appl. No. 15/898,206.

* cited by examiner

*Primary Examiner* — Qiuwen Mi
(74) *Attorney, Agent, or Firm* — Byrne Poh LLP; Nina R. Horan

(57) ABSTRACT

The disclosure provides compositions and methods for promoting hair growth and reducing hair loss using bioactive extracts of curcumin, *Withania somnifera*, and saw palmetto. Tocotrienols, tocopherols, piperine extract, low molecular weight collagen, and hyaluronic acid are optionally included in the compositions and methods

9 Claims, 9 Drawing Sheets

| Time Elapsed (months) | Composition taken | Range of Avg. Daily Hair Loss | Quality of Hair |
|---|---|---|---|
| 0 | Nothing taken | 200-300 | Wiry, dry, frizzy |
| 1 | 200 mg Curcumin, 5 mg piperine | 200-300 | Wiry, dry, frizzy |
| 2 | 200 mg Curcumin, 5 mg piperine | 150-200 | Wiry, dry, frizzy |
| 3 | 200 mg Curcumin, 5 mg piperine | 100-150 | Hair slightly thicker |
| 4 | 200 mg Curcumin, 5 mg piperine, 250 mg Withania somnifera | 50-100 | Hair attached more strongly at the root (less falls out when pulling gently on handful of scalp hair), new vellus hair growth |
| 5 | 200 mg Curcumin, 5 mg piperine, 250 mg Withania somnifera, 640 mg Serenoa repens | <50 | Less wiry, smoother, less brittle, significant new growth at the frontal hairline |
| 6 | 200 mg Curcumin, 5 mg piperine, 250 mg Withania somnifera, 640 mg Serenoa repens, 100 mg Tocotrienol/Tocopherol complex | <50 | Hair smoother, much less brittle & frizzy, continuing new vellus hair growth |
| 7 | 200 mg Curcumin, 5 mg piperine, 250 mg Withania somnifera, 640 mg Serenoa repens, 100 mg Tocotrienol/Tocopherol complex, 1000 mg of Hydrolyzed Collagen Types I and III, 100 mg Hyaluronic Acid | <50 | Hair denser and fuller, continuing new hair growth moving the receded frontal hairline further down |

FIGURE 3

FIG. 6A 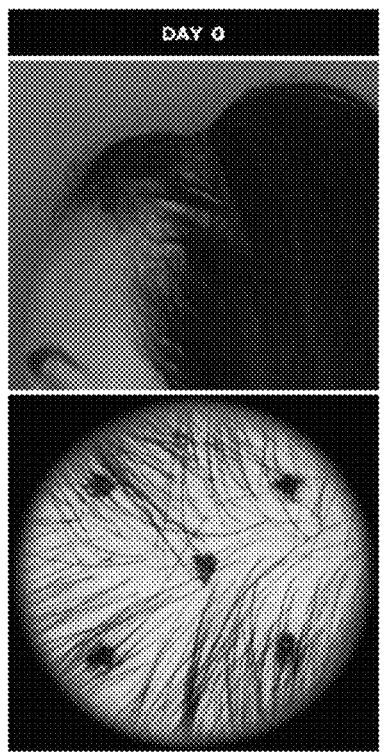 FIG.6C 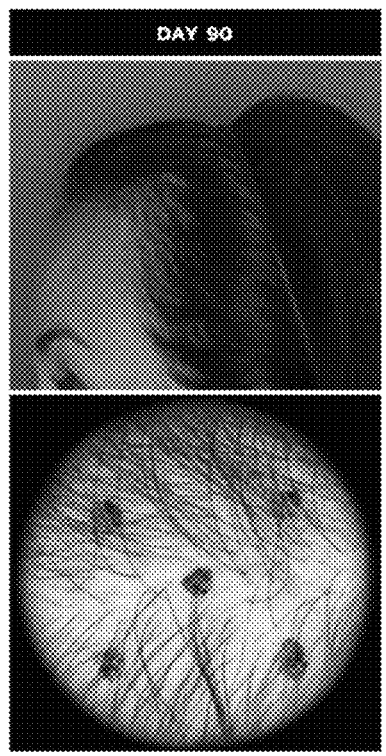 FIG. 6E 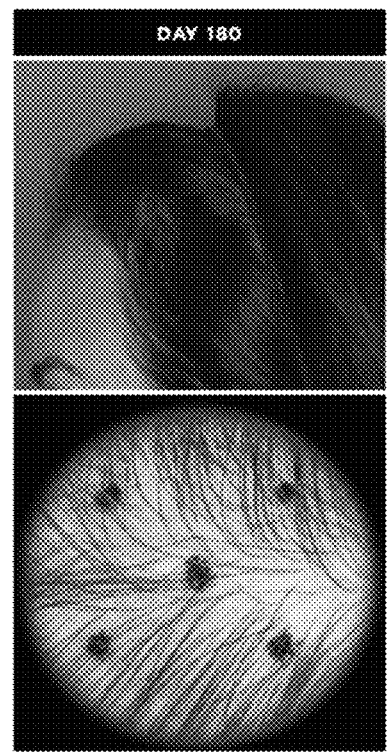
FIG. 6B FIG.6D FIG. 6F

COMPOSITIONS AND METHODS FOR HAIR REGROWTH

Throughout this application various publications are referenced. The disclosures of these publications in their entireties are hereby incorporated by reference into this application in order to more fully describe the state of the art to which this invention pertains.

FIELD OF THE INVENTION

The present disclosure relates to the field of hair loss, and more particularly to the restoration of hair growth.

BACKGROUND OF THE INVENTION

Hair loss (alopecia) is a widespread problem affecting about 80 million men and women in the United States alone according to the American Academy of Dermatology. The $7 billion hair loss industry is a testament to the significance and the scope of the issue. The most common alopecias are androgenic alopecia, telogen effluvium and alopecia areata.

Androgenic alopecia (AGA) is the most common type of hair loss in both sexes, affecting at least 50% of men by the age of 50 and up to 40% of women in mid-adult life. More recently AGA is being referred to as male pattern hair loss (MPHL) and female pattern hair loss (FPHL) to reflect the differences in clinical presentation and the new science on the pathophysiology of the conditions, which support the modern understanding that hair loss is due to the contribution of other factors, besides androgens and genetic disposition, particularly in FPHL.

In humans, individual hair follicles progress through phases of growth independent of one another. They are subject to and respond individually to the influence of several inductive and inhibitory signaling molecules in the follicle environment. Anagen, the growth phase, generally lasts between 2 to 7 years in a healthy follicle. Catagen is a transitional phase of regression that lasts approximately 2-3 weeks between the growth phase and the resting phase. Telogen, the resting phase, lasts for approximately 3 months. The late stage of telogen is associated with the regeneration of the next growth phase. Loss of coverage, or hair thinning and hair loss, occurs when the normal cycling and growth of numerous follicles are disrupted. The disruption can be widespread, sudden and synchronized causing immediately visible loss or it can be slow, steady and unsynchronized, becoming visible over a long period of time, only when 50% of the follicles have been affected. Hair density and volume decreases when the hair growth cycle is disrupted and more follicles enter catagen and telogen prematurely, while not enough follicles enter anagen to replace them. Further, miniaturization, the signature pathology seen in patients with MPHL & FPHL, can occur where the width of hair fibers progressively decrease in each consecutive cycle causing once thick and long hair fibers to become thinner, lighter, barely visible vellus-like hairs.

A modern view on alopecia describes all hair loss, regardless of its various manifestations and traditional classifications, as the result of a 'disordered hair follicle.' (Breitkopf, T., Dermatol. Clin., 2013, 31(1):1-19). When hair follicles on the scalp are in an unbalanced disordered state, it compromises their function and manifests in hair growth and cycle abnormalities. Different combinations of abnormalities pertain to different disorders. The traditional view held by researchers and clinicians considers hair loss as a disease, which has led to alopecias being classified by their presumed respective causes and/or manifestations. For instance, MPHL/FPHL and telogen effluvium (TE) are classified as non-inflammatory, whereas alopecia areata (AA) and scarring alopecias are classified as inflammatory diseases. Recent findings have begun to challenge this perspective as researchers have found that even in MPHL/FPHL there is significant evidence of micro-inflammation, a term proposed to reflect the indolent inflammatory process in AGA. (Mahe, Y. F., Int. J. Dermatol., 2000, 38(8):576-84). Thus, it is being recognized that in all alopecias there are multiple combinations of factors, like inflammation, that underlie the disordered hair follicle.

The hair growth cycle is primarily maintained through the complex interplay of numerous cytokines, growth factors and transcription factors that signal the cells of the follicles to either induce or prohibit hair growth. These signals are both introduced extrinsically and also produced intrinsically by the follicle's dermal papilla cells (DPCs) that determine follicle and hair fiber characteristics. Those extrinsic controls that induce early catagen and inhibit growth, such as the androgen dihydroxytestosterone (DHT), have provided targets for therapies, such as the drug finasteride in the case of DHT. However, even extrinsic factors act on the follicles by altering the production of signaling molecules by the follicle DPCs. The significance of immune signaling and balance in sustaining proper follicle functioning is further underscored by the fact that it represents one of the few sites of 'immune privilege' (IP) in the body. The follicle's IP normally protects the follicle from immune system recognition and inflammatory attack. IP also works to sequester anagen-associated autoantigens within the follicle, protecting them from immune recognition. Studies have shown that the follicle's IP can be compromised by stress-induced neuropeptides such as Substance P (SP) (Peters, E. M., Am. J. Pathol., 2007, 171(6):1872-86) and cytokines such as interferon gamma (IFN-γ). (Xing, L., Nat. Med., 2014, 20(9):1043-49). Subsequent to this immune system imbalance and collapsed IP, compromised follicles are subject to inflammatory attack. Thus, for a follicle to not become 'disordered' and to produce healthy hair, it is vital to maintain an IP.

Inflammatory responses can be further stimulated by the presence of free radicals, also referred to as Reactive Oxygen Species (ROS). ROS are highly reactive molecules with unpaired electrons that can directly damage cellular structures and alter DNA. They are generated endogenously through normal and specific metabolic processes and we are subject to ROS exposure from the environment, for instance in the form of common air pollutants. However, with age, the body's ability to neutralize ROS decreases since production of antioxidant enzymes and endogenous antioxidants decreases with age while ROS generation increases with age resulting in increased oxidative stress on the body, including hair. Compromised hair follicles are known to be particularly vulnerable to ROS from environmental stressors. Further, inflammatory responses, through positive feedback, create a cyclic cascade and generate even more ROS. For example, it has been shown in androgen induced alopecia that the generation of ROS mediates the pro-inflammatory androgen signaling cascade. Similarly, in models of chronic stress, the neurogenic inflammatory pathways of SP were shown to increase ROS and decrease innate antioxidant defenses, leading to hair growth arrest and hair cycle arrest.

Thus, the common underlying pathway of hair loss can be seen as disordered immune signaling and an oxidative imbalance that involve numerous players: pro-inflammatory cytokines, pro-fibrotic and growth inhibiting factors like TGF-β, and inflammatory cells—all perpetuated through chronic generation of free radicals, oxidative stress and further inflammatory changes and immune imbalances. This common pathway in hair loss can be triggered and propagated by several factors including, but not limited to: sudden changes or severe imbalances in nutrition as in crash diets, androgens, genetics, and stress.

Androgens, like other steroid hormones, act on target cells by diffusing through the plasma membrane, binding to specific receptors and then acting on the DNA, inducing the transcription and translation of specific hormone-regulated genes and their products, such as cytokines. In the follicle, testosterone is mostly metabolized by 5α-reductase (5-ar) into DHT. DHT is implicated in the pathogenesis of several androgen responsive disorders such as prostate disease, acne and AGA. It is now recognized that the effects of androgens within follicles are mediated via signaling cascades, which are dysregulated in pathologies like hair loss. The main action of DHT on follicles occurs within the dermal papilla cells, where it binds to androgen receptors, enters the nucleus and leads to increased transcription and overproduction of growth-inhibiting molecules like the cytokine TGF-β that signals catagen induction and apoptosis. Once triggered by minimal amounts of DHT, other factors can maintain the pathophysiology of AGA without the presence of androgens, as seen in men with MPHL who were castrated after puberty. Thus, it appears that blocking androgens alone to combat hair loss is insufficient due to the presence of signaling and dysregulation of the immune balance downstream of the initial insult, triggering a cascade of numerous immune and inflammatory processes that can sustain the alopecic pathway. In fact, androgen-induced overproduction of TGF-β by the DPC's and surrounding fibroblasts also plays a role in perifollicular fibrosis and inflammation—implicated in the pathophysiology of miniaturization in follicles. Of special note, MPHL and FPHL differ in that women have less total 5-ar than men. This may account for why current drug therapies that block 5-ar to treat alopecia produce minimal results in women as compared to men, especially given that systemic DHT and 5-ar are generally within normal limits in women with FPHL.

Stress has long been disputed as playing a measurable role in hair loss. Recent research, however, has begun to examine the roles of psycho-emotional stress, nerves and immune cells in hair growth and has discovered new pathways that link the central nervous system with the hair follicle. New evidence provides definable neurological, neuroendocrine and immunological mechanisms through which stress can inhibit hair growth. Psycho-emotional stress results in systemic elevation of nerve growth factor, a key modulator of hair growth termination, and substance P (SP), the prototypic stress-associated neuropeptide that is widely acknowledged as a potent modulator of immune responses and neurogenic inflammation of the skin. In addition to compromising follicle IP, elevated levels of SP induce the proliferation and degranulation of local mast cells and these mast cells in turn release a host of pro-inflammatory mediators like histamine and cytokines like TNF-α. The resulting neurogenic inflammation has been shown to cause hair growth arrest and promotion of follicle regression. The follicle has also been shown to be highly sensitive to stress hormones like cortisol, which are known to cause catagen induction, and the follicle even contains all the needed machinery to self-produce these hormones. Specifically, one of the major stress hormones, corticotropin-releasing hormone (CRH), is elevated systemically during stress and can bind to the follicle, which induces the follicle to produce even more CRH and cortisol.

There are limited options regarding pharmaceutical therapeutics for the treatment of AGA in the United States, and only one is indicated for FPHL. One therapeutic, is minoxidil. While minoxidil's mechanism of action has not been clarified despite its use since 1988 in the treatment of AGA, it is widely believed to elongate the anagen phase by acting on potassium channels in the hair follicle, thereby improving follicular circulation. Some known side effects of minoxidil are dizziness, chest pain, difficulty breathing and swelling. The topical version has the further side effects of causing rashes and skin irritations in some users. The other FDA-approved therapeutic, finasteride, is only indicated in MPHL. It works by competitively binding the enzyme 5-ar, thereby reducing the conversion of testosterone into DHT, which is a known androgen trigger for hair loss. Finasteride is FDA-approved for treatment of AGA only in men and has also been reported to cause side effects of erectile dysfunction, ejaculatory dysfunction and loss of libido in a segment of users.

The complexity of the hair loss pathway requires a multi-pronged approach to treat the most prominent aspects of the problem. Pharmaceutical therapies such as minoxidil and finasteride achieve some success in treating hair loss, but ultimately only address single elements of a larger problem, not addressing downstream dysregulated signaling or the common pathway of inflammation and oxidative stress. Additionally, they are associated with potential significant and debilitating side effects. There is a need for a therapy which in addition to addressing just one trigger, like androgens, also addresses the disordered immune signaling of catagen-inducing cytokines and addresses the inflammation that is both a result and a promoter of the disordered signaling. An ideal therapeutic should further address the generation and effect of ROS in hair loss due to the role of oxidative stress in aggravating inflammation. And, importantly, there is a need for a therapy which can also address psycho-emotional stress and its effects on hair loss. Finally, there is a need for a therapy that is safe and does not induce similar side effects.

Nutraceutical formulations and the multi-targeting bioactive properties of certain plant phytonutrients offer a possible solution since they can target multiple triggers of hair loss at once. Further, the fact that these phytonutrients are natural in origin and known to be safe for consumption avoids many of the concerns of undesired side effects, which are common with pharmaceuticals.

One such phytonutrient is curcumin (diferuloyl methane) which is found in the rhizome of the turmeric plant, *Curcuma longa*, and is readily extracted from the plant, U.S. Pat. No. 5,861,415. Curcumin has been shown to slow hair loss by down-regulating expression of the DHT-binding Androgen Receptor, inhibit type II 5-ar, support regrowth by decreasing levels of the catagen-signaling cytokine TGF-β and to be a potent antioxidant and anti-inflammatory agent. (Pumthong, G., J. Dermatolog. Treat., 2012, 23(5):385-92). It has significant activity against pro-inflammatory cytokines like TNF-α and IL-1, both known to signal catagen and to inhibit follicle growth. Curcumin's anti-stress and neuroprotective properties have been studied extensively and one neurotransmitter it inhibits is Substance P, which in high levels has been shown to compromise the follicle's immune privilege and to induce mast cell degranulation that leads to catagen, hair growth inhibition and increased inflammation. As for its safety profile, curcumin has not been shown to evidence toxicity in human studies at doses of up to 8000 mg daily for three months. (Cheng, A. L., Anticancer. Res., 2001, 21(4B):2895-2900).

Another phytonutrient is *Withania somnifera*, commonly known as Ashwagandha. It is a medicinal plant that has been employed for centuries in ayurvedic medicine and has recently been observed to reduce hair loss. (Kalani, A., BMJ Case Rep., 2012). Ashwagandha has also been recognized as an adaptogen, a unique class of herbal ingredients that result in the restoration of normal physiological function (homeostasis), and to increase the body's resistance to the effects of stress, such as by decreasing cellular sensitivity to stress. Ashwagandha is known to rebalance and lower the levels of the stress hormone cortisol, to improve thyroid function, and to elevate the body's endogenous antioxidant enzymes through its principal withanolides. Ashwagandha also exhibits inhibitory effects on pro-inflammatory cytokines such as IL-6 and TNF-α. The active compounds in *Withania somnifera* leaves and roots are C28 steroidal lactone molecules known as withanolides, such as Withaferin A, and are extracted from the plant using known methods, U.S. Pat. No. 7,108,870.

Extracts of *Serenoa repens* or "saw palmetto," a dwarf palm tree, have been observed to help hair regrowth in male pattern baldness. (Chittur, S., Evid. Based Complement Alternat. Med., 2011:985345). The saw palmetto berry contains over 100 known compounds. The active ingredients in saw palmetto are contained in the purified lipid soluble extract of the saw palmetto berry. This has been found to contain 85 to 95 percent fatty acids (predominantly lauric, caprylic, and caproic), long chain alcohols, and sterols (including beta-sitosterol, stigmasterol, cycloartenol, lupeol, lupenone, and methylcycloartenol). Saw palmetto naturally inhibits the activity of the testosterone catalyzing 5-ar enzyme, but unlike the drug finasteride it does not interfere with Prostate Specific Antigen levels. In comparative studies with finasteride, saw palmetto was even associated with an improvement of sexual dysfunction. (Suter, A., Phytother. Res., 2013, 27(2):218-26). The berries also contain high molecular weight polysaccharides (sugars), which may reduce inflammation or strengthen the immune system.

Tocotrienols, together with tocopherols, which are members of the Vitamin E family, possess potent antioxidant activity by directly neutralizing reactive oxygen species and also raising the body's own antioxidants and antioxidant enzymes. Tocotrienols have also been shown to provide protection against UV light and oxidative stress and to promote hair regrowth in humans. (Beoy, L. A., Trop. Life Sci. Res., 2010, 21(2):91-99). A natural source rich in tocotrienols and tocopherols is palm oil, with crude palm oil (also referred to as the "tocotrienol-rich fraction") containing up to 800 mg/kg weight of α- and γ-tocotrienol isotypes. The distribution of vitamin E in palm oil is 30% tocopherols and 70% tocotrienols. Natural sources of vitamin E, such as palm oil, are believed to have greater bioactivity than synthetically manufactured vitamin E.

Piperine, the active principle of the dried, unripe fruits of various black pepper plants, is an alkaloid which has been shown in in vitro studies to protect against oxidative damage by inhibiting or quenching free radicals and reactive oxygen species. It has also been shown to enhance the bioavailability of a number of therapeutic drugs and phytonutrients like curcumin by strongly inhibiting hepatic and intestinal aryl hydrocarbon hydroxylase and UDP-glucuronyl transferase. (Srinivasan, K., Crit. Rev. Food Sci. Nutri., 2007, 47(8): 735-48). In addition to possessing antioxidant properties, piperine has further been shown to possess analgesic and anti-inflammatory properties in animal studies. (Tasleem, F., Asian Pac. J. Trop. Med., 2014, 7S1:S461-8).

Healthy thyroid function is crucial to the metabolism of almost all tissues, hair follicles included. The metabolic effects of the thyroid come from two iodine containing-hormones, triiodothyronine (T3) and thyroxine (T4). Hair follicles (HFs) are very sensitive to thyroid hormones (Stenn K S., Physiol Rev. 2001 81:449-94.). Research has shown that human scalp hair follicles are direct targets for TSH thyroid stimulating hormone (TSH) which has various functions that benefit hair growth (Bodo E., Journal of Investigative Dermatology. 2009 129: 1126-1139). TSH also directly upregulates the "master antioxidant" glutathione peroxidase and mitochondrial transcription factors in human dermal papillae fibroblasts further supporting a role for TSH signaling in HF metabolism and oxidation processes (Id). Thyroid hormones also induce substantial modifications in mitochondrial inner membrane protein and lipid compositions that are involved in mitochondrial biogenesis. (Harper, M E., Thyroid. 2008; 18(2):145-56). It has been reported that inhibition of mitochondrial protein synthesis can increase an area of hair loss by 30-80% (Hyde, G E., Otolaryngology—Head and Neck Surgery. 1995; 113:530-540).

The hair follicle also has a high affinity for environmental pollutants such as toxins and some of these toxic chemicals are stored in the keratinized structures at the hair follicle (Pierard, G E., Journal of Cutaneous Pathology, 1979:6: 237-24). Hair loss patterns, such as diffuse alopecia, are directly related to ingestion, subjection, and accumulation of toxic metals from the environment. Mercury is an example of one such heavy metal that can cause hair loss by accumulating in the thyroid and subsequently reducing iodide uptake at the sodium/iodide symporter by binding to iodide; decreasing the rate of synthesis of thyroid hormones (Chen, A., Environ Health Perspect., 2013 February; 121(2): 181-186).

In addition to being a necessary factor in healthy thyroid function, iodine is known as one of the best natural chelators in our body as it binds to toxic metals to form complex structures which are easily excreted from the body (H SGK., Marcel Dekker Inc. 1988). As an example, iodine has the ability to increase mobilization of bromine from storage sites resulting in increased urinary excretion of bromide (Sircus, D M., Lulu Press; 2016). By chelating toxins from the body, iodine allows minerals that are essential to our hair health, such as selenium, to support the hair growth cycle. Iodine is a component of kelp, and of all species of kelp it is found in the highest concentration in the species *Laminara digtata*.

Iodine is one component of kelp, and of all species of kelp it is found in the highest concentration in the species *Laminara digtata*. Kelp includes several other vitamins and minerals necessary for an optimal hair growth cycle. One of these minerals is choline. It was found that the addition of choline to a bioavailable form of silica improved the tensile strength (elasticity and break load) of hair and resulted in thicker hair (Wickett R R., *Arch Dermatol Res.* 2007 December; 299(10):499-505). Calcium is another component of kelp that has beneficial effects for hair. Calcium has the ability to not only interact with signal pathways that are essential to hair growth but to also activate hair follicle stem cells that are in rest, quiescence, in order for growth to occur (Yucel, G., Genes Dev. 2013: 27(11). 1217-22). Copper can also be found in kelp. Copper plays a role in the differentiation and proliferation of dermal papilla cells, which are specialized fibroblasts that play an important role in the development of hair follicles (Kil M., Ann Dermatol. 2013: 25(4) 405-409).

It is an object of the present disclosure to provide a nutraceutical supplement composition that simultaneously inhibits the molecular triggers of hair loss associated with stress and androgens and further addresses the concurrent cascade of disordered cytokine signaling, inflammation and oxidative damage that is brought on by their activity, thereby preventing damage and shrinkage to hair follicles and promoting more follicles to enter a healthy hair cycle in a multi-targeted, comprehensive manner.

Citation of any reference in this section of the present disclosure is not to be construed as an admission that such reference is prior art to the present disclosure.

SUMMARY OF THE INVENTION

Accordingly, the present disclosure provides a composition for promoting hair growth and reducing hair loss, comprising from about 100 to about 1000 mg of an extract of *Curcuma longa*, from about 100 mg to about 1000 mg of an extract of the roots and leaves of *Withania somnifera*, and at least about 200 mg of saw palmetto extract. Advantageously, the composition further comprises from about 100 mg to about 1000 mg of tocotrienols and tocopherols. The composition may further comprise from about 225 mcg to about 300 mcg of iodine. The composition may further comprise low molecular weight collagen and hyaluronic acid and the collagen may be Type I and Type III collagen and have a molecular weight of less than about 5000 daltons. The collagen may be present in an amount from about 500 mg to about 2000 mg, and said hyaluronic acid may be present in an amount from about 100 mg to about 1000 mg.

The composition of the disclosure may further include at least about 200 mg of curcumin, at least about 100 mg of withanolides, at least about 200 mg of saw palmetto extract, at least about 225 mcg of iodine, and at least about 100 mg of tocotrienols and tocopherols comprising a complex of about 78% tocotrienols and about 22% tocopherols, at least about 1000 mg of Type I and III collagen having a molecular weight of less than about 3000 Daltons, and at least about 100 mg of hyaluronic acid.

The composition of the disclosure may further include at least about 5 mg of piperine.

The composition of the disclosure may further include one or more compounds from the group consisting of green tea extract, L-methionine, L-cysteine hydrochloride, resveratrol, capsaicin, biotin, selenium, Vitamin D, Vitamin A, and Vitamin C.

The disclosure provides a food item comprising a composition as described herein, and a mixture of additional components selected from the group consisting of vitamins, amino acids, minerals, proteins, carbohydrates, fats, flours, flavoring, and sweetener.

The disclosure also provides a method of promoting hair growth and reducing hair loss by administering to a subject an effective amount of a composition as described herein, in a pharmaceutically suitable vehicle, for a time sufficient to promote hair regrowth and reduce hair loss in subjects exhibiting symptoms of alopecia.

Additional features, advantages, and aspects of the present disclosure are set forth or apparent from consideration of the following detailed description, drawings, and claims. Moreover, it is to be understood that both the foregoing summary of the present disclosure and the following detailed description are exemplary and intended to provide further explanation without limiting the scope of the present disclosure as claimed.

BRIEF DESCRIPTION OF THE DRAWINGS

The accompanying drawings, which are included to provide a further understanding of the present disclosure, are incorporated in and constitute a part of this specification, illustrate aspects of the present disclosure and, together with the detailed description, serve to explain the principles of the present disclosure. In the drawings:

FIG. 3 is a table depicting the subject's results of various implementations of the disclosure over a 7-month period.

FIG. 5A shows the terminal hair count at baseline, 3 months and 6 months in the active group vs. placebo. FIG. 5B shows the vellus hair count at baseline, 3 months and 6 months in the active group vs. placebo. FIG. 5C shows hair growth global improvement by investigator grading at 3 months and 6 months in the active group vs. placebo. FIG. 5D shows hair quality global improvement at 3 months and 6 months in the active group vs. placebo.

FIG. 6A-FIG. 6F show images of an active subject at baseline (FIGS. 6A and B), 3 months (FIGS. 6C and D) and 6 months (FIGS. 6E and F).

DETAILED DESCRIPTION OF THE INVENTION

The present disclosure provides novel nutraceutical compositions which have been shown to reduce hair loss and promote the growth of new hair in individuals suffering from various types and degrees of hair loss. Current treatments for hair loss and promotion of hair growth fall under two categories: a) pharmacological or b) nutrient supplements. Pharmacological treatments come with the risk of significant side effects and nutrient supplements only provide nutrition while ignoring the ongoing causes of the actual hair loss itself. A non-pharmacological nutraceutical formulation, such as the compositions described herein, provides a much needed option for those who suffer hair loss, since it both addresses the underlying causes of hair loss using natural remedies without pharmacological side effects and provides the nutrition needed for improved hair growth. It can further be used as both a preventative and as a complementary therapy to augment pharmacological treatments.

Figure 1:
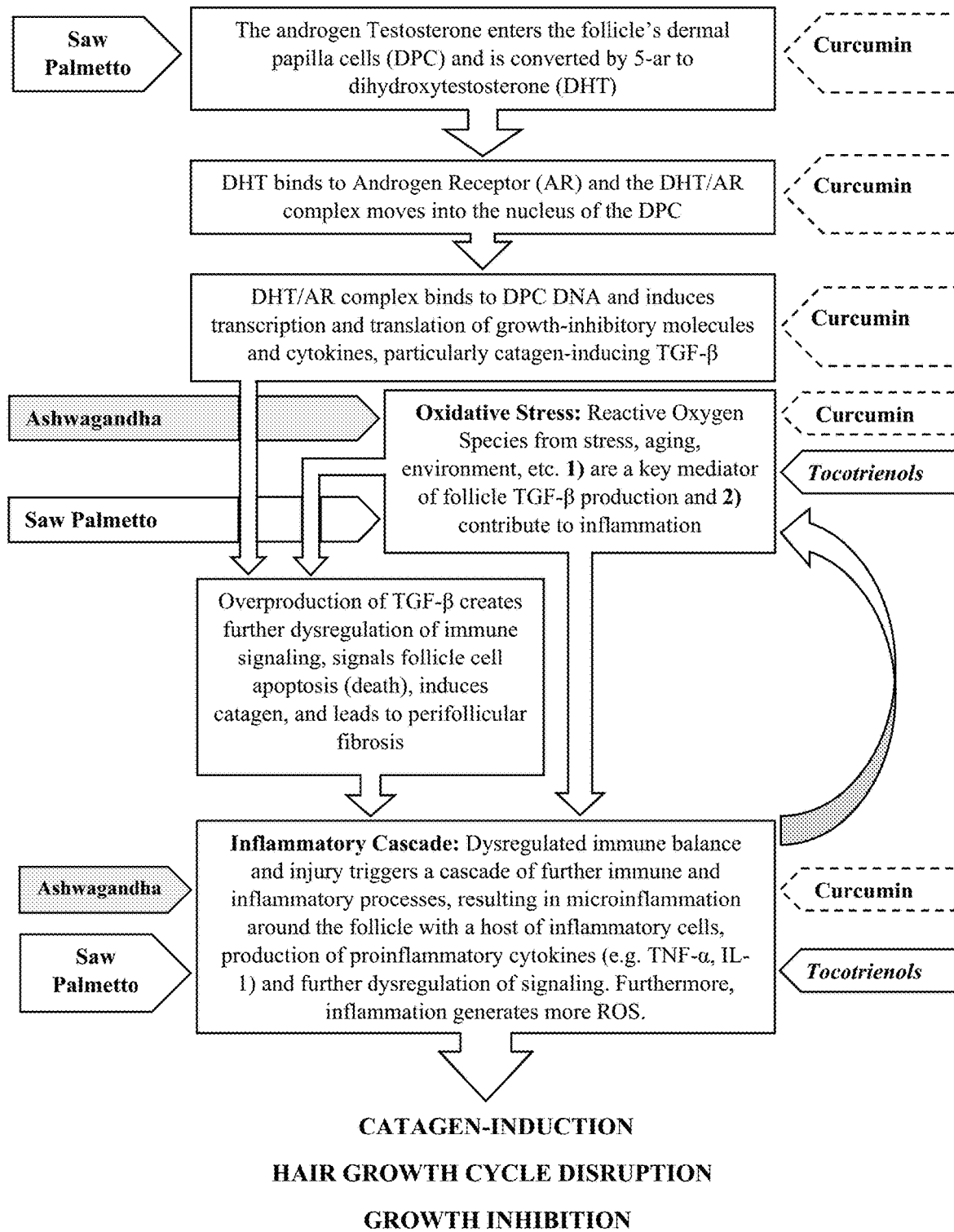
FIG. 1 depicts the androgen pathway and indicates where components of the disclosure help mitigate damage to hair follicles.
Figure 2:
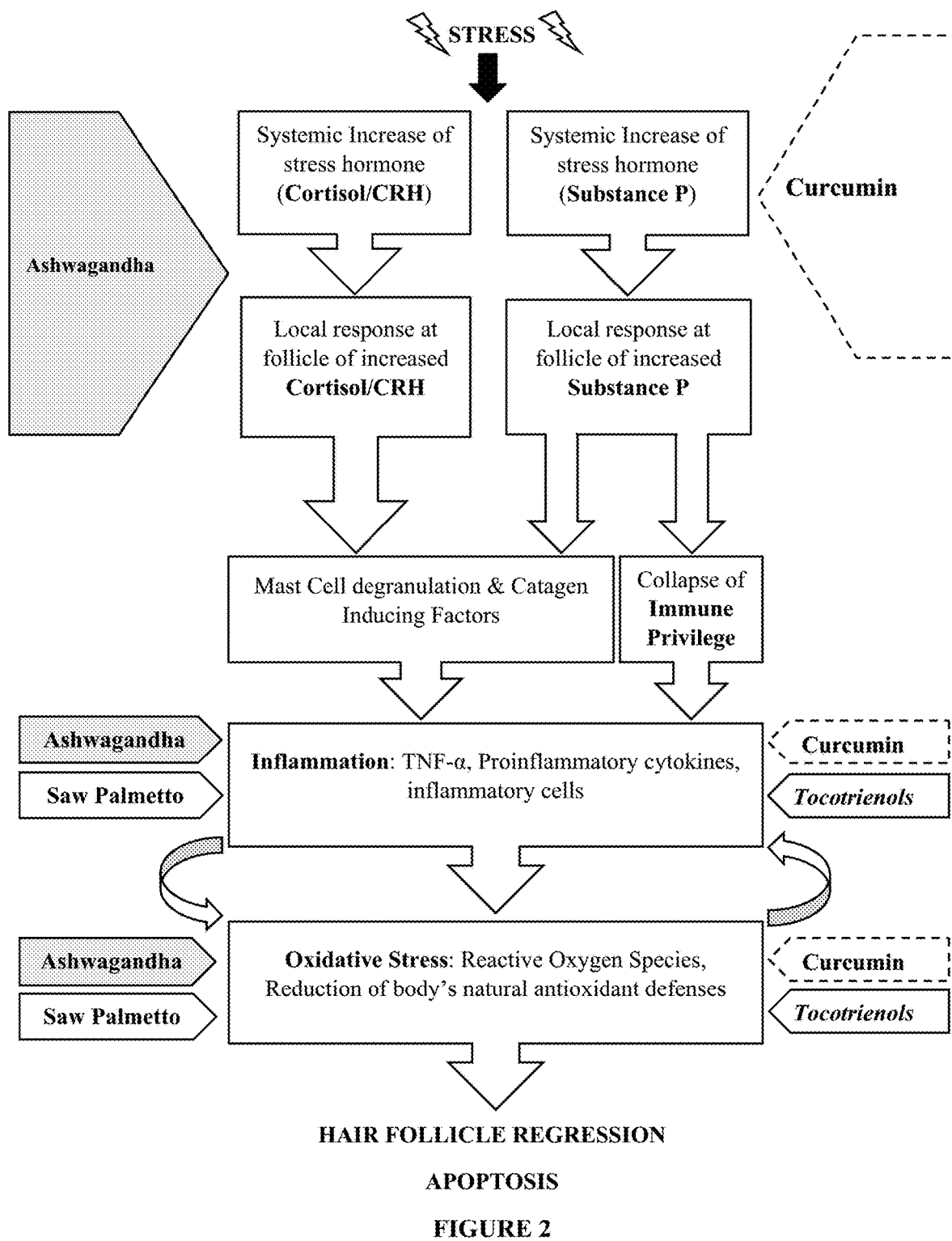
FIG. 2 depicts how the stress pathway may lead to hair loss and indicates where components of the disclosure help mitigate damage to hair follicles.

The present disclosure provides compositions and methods for promoting hair health and hair growth. Without being bound by any particular theory or explanation, the novel nutraceutical compositions of the disclosure contain components which may synergistically inhibit multiple triggers of hair loss such as DHT (see FIG. 1) and the stress hormone cortisol (see FIG. 2); reduce inflammation and oxidative stress associated with the self-sustaining common pathway of hair loss; and provide necessary nutrition which may be better absorbed and utilized by hair follicles after the follicles are rebalanced by the other components of the compositions of the disclosure.

In one implementation of the disclosure for promoting hair growth and reducing hair loss, the composition comprises curcumin, ashwagandha, and saw palmetto.

In another implementation of the disclosure for promoting hair growth and reducing hair loss, the composition comprises curcumin, ashwagandha, saw palmetto and iodine.

In a preferred embodiment for male subjects, the composition includes at least about 200 mg of curcumin, at least about 100 mg of withanolides, and at least about 500 mg of bioactive saw palmetto, preferably standardized to contain at least about 85% fatty acids and sterols.

In another preferred embodiment for hair regrowth and to reduce hair loss in female subjects, the composition of the disclosure further includes at least about 200 mg of bioactive saw palmetto extract, preferably standardized to contain at least about 85% fatty acids and sterols. This embodiment containing less saw palmetto is preferred in women due to the fact that women typically have about 5 times less total testosterone than men. The same benefits can be achieved with less of this DHT inhibitor since women have less testosterone which can be metabolized into DHT.

In a more preferred embodiment of the aforementioned compositions, the compositions can additionally contain one or more of an effective amount of an extract from saw palmetto, tocotrienols, tocopherols, iodine, piperine, low molecular weight collagen, and hyaluronic acid.

The saw palmetto extract is preferably a bioactive extract of the *Serenoa repens* plant. Methods for obtaining the bioactive components of the disclosure are known, for example, by extraction of plant materials, as described in U.S. Pat. No. 6,039,950. The components can further be obtained with increased bioactivity and/or bioavailability, using known methods for improving the bioavailability of bioactive components extracted from plants, resulting in the need for less of the bioactive component as described in U.S. Pat. Nos. 8,329,233, 6,153,198, and 5,891,465. The bioactive saw palmetto extract is further preferably standardized to contain at least 85% fatty acids and sterols.

The tocotrienols and tocopherols for use in the compositions of the disclosure may be combined in a complex containing about 78% tocotrienols and about 22% tocopherols by weight.

The iodine for use in the compositions of the disclosure may be obtained from kelp, e.g., *Laminara digitata*. In some embodiments, the iodine is isolated from kelp. In other embodiments, the iodine is provided by kelp.

The low molecular weight collagen is preferably hydrolyzed Type I and Type III collagen having a molecular weight of less than about 3000 daltons.

In one embodiment, the composition of the disclosure comprises from about 100 mg to about 1000 mg of an extract of *Curcuma longa*, from about 100 mg to about 1000 mg of an extract of the roots and leaves of *Withania somnifera*, at least about 200 mg of saw palmetto extract, and from about 225 mcg to 300 mcg of iodine.

In another embodiment, the composition of the disclosure comprises at least about 200 mg of curcumin, at least about 100 mg of withanolides, at least about 500 mg of bioactive saw palmetto, preferably standardized to contain at least about 85% fatty acids and sterols, and one or more of the following: at least about 200 mg of saw palmetto extract, about 10 mg to about 1000 mg of tocotrienol and about 50 mg to about 1000 mg of tocopherols present in a complex comprised of about 78% tocotrienols and about 22% tocopherols, at least about 225 mcg of iodine, at least about 5 mg of piperine, about 500 mg to about 2000 mg of hydrolyzed Types I and III collagen having a molecular weight of less than about 3000 daltons, and/or about 100 mg to about 1000 mg of hyaluronic acid.

For female subjects an implementation of a composition of the disclosure may contain at least about 200 mg of curcumin, at least about 100 mg of withanolides, and at least about 200 mg of bioactive saw palmetto, preferably standardized to contain at least about 85% fatty acids and sterols, and one or more of the following: at least about 200 mg of saw palmetto extract, about 10 mg to about 1000 mg of tocotrienol and about 50 mg to about 1000 mg of tocopherols present in a complex comprised of about 78% tocotrienols and about 22% tocopherols, at least about 225 mcg of iodine, at least about 5 mg of piperine, about 500 mg to about 2000 mg of hydrolyzed Types I and III collagen having a molecular weight of less than about 3000 daltons, and/or about 100 mg to about 1000 mg of hyaluronic acid.

The compositions of the disclosure may also include one or more of the following ingredients: green tea extract, L-methionine, L-cysteine hydrochloride, resveratrol, capsaicin, biotin, selenium, Vitamin D, Vitamin A, Vitamin C, choline, calcium, and/or copper.

The disclosure further provides a method of promoting hair growth and reducing hair loss in a subject experiencing hair loss of the scalp, by administering to the subject an effective amount (e.g. an amount effective to promote hair regrowth, slow the progression of hair loss, etc.) of said composition comprising at least about 200 mg of curcumin, at least about 100 mg of withanolides, and at least about 200 mg of bioactive saw palmetto, preferably standardized to contain at least about 85% fatty acids and sterols, and one or more of the following: at least about 200 mg of saw palmetto extract, about 10 mg to about 1000 mg of tocotrienol and about 50 mg to about 1000 mg of tocopherols present in a complex comprised of about 78% tocotrienols and about 22% tocopherols, at least about 225 mcg of iodine, at least about 5 mg of piperine, about 500 mg to about 2000 mg of hydrolyzed Types I and III collagen having a molecular weight of less than about 3000 daltons, and/or about 100 mg to about 1000 mg of hyaluronic acid.

The compositions and method of the disclosure for alleviating hair loss, may be effective to improve hair loss caused by, for example, forms of alopecia including androgenetic alopecia, alopecia areata, alopecia mucinosa, telogen effluvium, chronic inflammation, extreme and/or chronic stress, diabetes, cellulitis, hair treatments, hereditary disorders, hormonal changes, hyperthyroidism, hypothyroidism, malnutrition, lupus, medication side effects, including from chemotherapy and birth control, radiation, aging and trichotillomania.

In an implementation, the disclosure provides methods for the treatment and/or reduction of hair loss in a subject, comprising administering to the subject in a pharmaceutically suitable vehicle, an effective amount of a composition of the disclosure comprising at least about 200 mg of curcumin, at least about 100 mg of withanolides, and at least about 200 mg of bioactive saw palmetto, preferably standardized to contain at least about 85% fatty acids and sterols, and one or more of the following: at least about 200 mg of saw palmetto extract, about 10 mg to about 1000 mg of tocotrienol and about 50 mg to about 1000 mg of tocopherols present in a complex comprised of about 78% tocotrienols and about 22% tocopherols, at least about 225 mcg of iodine, at least about 5 mg of piperine, about 500 mg to about 2000 mg of hydrolyzed Types I and III collagen having a molecular weight of less than about 3000 daltons, and/or about 100 mg to about 1000 mg of hyaluronic acid. The compositions can additionally include further amounts of nutrients necessary and beneficial hair growth which are known to those having ordinary skills in the art.

"Pharmaceutically suitable vehicle" as used herein refers to a non-toxic solid, semisolid (also referred to as "softgel") or liquid filler, diluent, encapsulating material or formulation auxiliary of any type, suitable for the particular route of administration and desired release rate (e.g. immediate or controlled release) of the active compounds, and are well known in the art. Pharmaceutically suitable vehicles and excipients that may be used to formulate oral dosage forms are described in the Handbook of Pharmaceutical Excipients, American Pharmaceutical Association, Arthur H. Kibbe (2000), incorporated herein by reference in its entirety.

The bioactive compounds in the compositions of the disclosure may be combined in a single dosage form or for unit-dose or multi-dose administration. The compositions can be formulated into suitable preparations for administration to a subject, such as solutions, suspensions, tablets, dispersible tablets, capsules, powders, sustained release, for oral administration or in sterile solutions or suspensions for parenteral administration, as well as transdermal patch preparation, nasal formulation and dry powder inhalers et al. The compositions may also be formulated as liquid dosage forms such as elixir, suspension or syrup. The compositions are formulated into compositions using techniques and procedures well known in the art.

Dosage of the therapeutic agent(s) of the disclosure is dependent upon many factors including, but not limited to, the severity of the hair loss, the subject's age, general health and individual response to the compositions of the disclosure. Accordingly, dosages of the compositions can vary and be readily adjusted, depending on each subject's response.

In one implementation of the disclosure, the compositions of the disclosure may be administered to a subject in an amount of at least approximately 1800 mg per day as a single dose, or may be divided into two or more dosages administered throughout a 24 hour period. Ingesting at mealtimes may improve absorption of some of the components of the compositions of the disclosure. The time of day the given dose or fraction of the given dose is administered can vary by day. The compositions of the disclosure may be taken on a daily basis until desired hair growth is achieved, or indefinitely.

In addition to oral dosage forms, the compositions of the disclosure may be incorporated with other ingredients into food, for example by adding the compositions to mixtures used to prepare a "food bar," cookie, cake or other edible item. Mixtures of ingredients for preparing nutrition bars and other baked and non-baked items are known. Flavoring and sweetener may be added to mask any "medicine taste" of the compositions of the disclosure. Preservatives may be added to improve shelf life.

In accordance with the practice of the disclosure, the subject may be a human. The subject may also be a mammal, such as a monkey, ape, dog, cat, cow, pig, horse, sheep, rabbit, mouse, rat or a bird.

The person of ordinary skill in the art will recognize that additional ingredients can be used in the compositions and methods of the present disclosure, for example to promote hair health and appearance, while maintaining effectiveness or enhancing the activity of the compositions in promoting hair growth and reducing hair loss.

Example 1

The male subject was a 49-year old male. He began to notice mild hair thinning at the age of 28. However, the hair loss became significantly more pronounced after he underwent radiation therapy for thyroid cancer at the age of 32. Over the next 17 years, he went to numerous physicians and took the only FDA-approved pharmaceuticals for hair loss (minoxidil and finasteride) but the improvement was minimal and didn't stall his progression to Stage III Vertex/Stage IV MPHL on the Hamilton-Norwood scale. During this time he also tried several natural supplements and topical formulations, but did not see any noticeable improvement. Prior to taking the implementations of the disclosure described herein, he had taken *Serenoa repens* alone and biotin alone, which did not result in a noticeable cessation of hair loss or new hair growth. In 2012 he was additionally diagnosed with Rheumatoid Arthritis (RA), which is an autoimmune condition that creates a pro-inflammatory state in the body and significantly affects joints. The subject was also suffering from chronic stress at this time. The subject notes that as a result of his condition his hair loss and the quality of his hair also worsened.

The subject was first given Curcumin extracted from *Curcuma Longa* standardized to 95% Curcuminoids including: curcumin, desmethoxy curcumin, bis-desmethoxy curcumin and volatile oils of turmeric rhizome (BCM-95®, Dolcas-Biotech, LLC, Chester, N.J.) in amounts of at least 200 mg a day. To improve curcumin absorption and bioavailability, it was taken together with 5 mg of standardized extraction of piperine. After continuing this regimen for 3 months and in addition to improvement of his RA symptoms, he noted decreased hair shedding and slightly improved hair thickness and quality. During month 4, the subject was additionally given a daily 250 mg dose of Ashwagandha extracted from *Withania somnifera*, containing at least 8% withanolide glycosides and 32% oligosaccharides from the roots and leaves (Sensoril®, Natreon, New Brunswick, N.J.) for stress associated with his condition and work. He noted that month that there was a further decrease in his hair loss and some small growth of new hairs. During month 5, the subject was additionally given a daily dose of Certified Organic saw palmetto extract Standardized 85-95% fatty acids (Valensa Eustis, Fla.) in the amount of 640 mg a day. During that month he experienced significant new growth at the frontal hairline and temples, a decrease in hair loss and improvement in hair quality. During month 6, the subject added a 100 mg dose of tocotrienol/tocopherol complex comprising 78% tocotrienols and 22% tocopherols (Tocomax™ 20%, Carotech, Malaysia) a day. This addition lead to further improvement in new hair growth at the hairline and the vertex and his hair became less brittle and smoother. Lastly, in month 7, He was additionally given approximately 1000 mg of hydrolyzed marine collagen Types I and III (Youtheory, Tustin, Calif.) and 100 mg of hyaluronic acid (NOW Foods, Bloomingdale, Ill.). At the end of month 7 the subject reported improvement in hair density, thickness, and continued new hair growth. The subject's progression is tabulated in FIG. 3.

Before initiation of the experiment, the subject had a bald spot on his crown covering an area of approximately 78 cm$^2$. Upon evaluation after 7 months, the results showed that the progression of his hair loss and the recession of the frontal hairline were stalled. There was also notable and measurable new growth at the hairline, temples and vertex. The original bald spot had been reduced to an area of approximately 38 cm$^2$, or an increase of hair growth of approximately 40 cm$^2$. Further, there was increase in the thickness and overall quality of hair.

After having significant loss of scalp hair for a period of 17 years, the subject experienced significant new hair growth and overall increase in thickness of scalp hair. The subject experienced no noticeable side effects from consumption of the composition.

Example 2

The subject, a 36 year-old male with early stages of MPHL (stage II on the Hamilton-Norwood scale), began taking an implementation of the disclosure consisting of 200 mg curcumin, 5 mg of piperine, 250 mg of withanolides, 640 mg of *Serenoa repens,* 100 mg Tocotrienol/Tocopherol complex comprising 78% tocotrienols and 22% tocopherols, 900 mg of Hydrolyzed Collagen Types I and III, 100 mg Hyaluronic Acid, 5 mg Vitamin A, 3 mg Vitamin D, 60 mg Vitamin C, 0.2 mg Selenium, 3 mg Biotin, 5 mg Capsaicin, 50 mg Resveratrol, 100 mg L-Methionine and 100 mg L-Cysteine Hydrochloride. After 6 months of daily ingestion the composition, he not only noticed a halt to the progression of his alopecia, but he also noted new hair growth, especially in the front—filling in his receding hairline. His hair also became thicker and more manageable. His wife and colleagues noted the increased hair growth and thickness. He even decided to start growing his hair longer. Overall, he also noted that he was feeling overall much healthier and even experienced increased libido.

Example 3

The subject was a 51 year-old female with moderate to severe stage 2 (Ludwig scale) manifesting in typical female pattern hair loss—significant widening of the part, diffuse hair loss and thinning of the crown. She started noticing hair thinning and loss in her 20's and tried many different products, without improvement. She concurrently suffered from chronic stress. The subject began taking began taking an implementation of the disclosure consisting of 200 mg curcumin, 5 mg of piperine, 250 mg of withanolides, 200 mg of *Serenoa repens,* 100 mg Tocotrienol/Tocopherol complex comprising 78% tocotrienols and 22% tocopherols, 900 mg of Hydrolyzed Collagen Types I and III, 100 mg Hyaluronic Acid, 5 mg Vitamin A, 3 mg Vitamin D, 60 mg Vitamin C, 0.2 mg Selenium, 3 mg Biotin, 5 mg Capsaicin, 50 mg Resveratrol, 100 mg L-Methionine and 100 mg L-Cysteine Hydrochloride daily. After a 6 month period, she saw dramatic improvement not only in quality and shine, but also saw significant hair growth within 7 months of use.

Example 4—Genemarkers™ Cytotoxicity & Cell Proliferation Analysis of Human Dermal Papillae Cells Treated with Test Materials for 24 or 48 Hours This study was conducted to determine the effect of test materials on cell proliferation of human follicular dermal papillae cells (DPCs). Two different types of assays were used to measure proliferation, MTT assay & BrdU ELISA.

Example 4.1—MTT Assay

The MTT cell proliferation assay measures cell proliferation rate and conversely when metabolic events lead to apoptosis, the reduction in cell viability. Cell viability is measured via the reduction of tetrazolium salts. The yellow tetrazolium MTT (3-(4, 5-dimethylthiazolyl-2)-2, 5-diphenyltetrazolium bromide) is reduced by metabolically active cells, in part by the action of dehydrogenase enzymes. The resulting intracellular purple formazan substance can be solubilized and quantified by spectrophotometry. MTT assays performed confirmed the viability and proliferation ability of DPCs in the presence of combinations of Ashwaghanda, Saw Palmetto, and Kelp.

Example 4.2—BrdU ELISA

Halogenated nucleotides such as pyrimidine analog 5-bromo-2'-deoxyuridine (BrdU) are incorporated into cellular DNA during cell proliferation using an anti-BrdU antibody. When cells are cultured with labeling medium that contains BrdU, the pyrimidine analog is incorporated in place of thymidine in newly synthesized DNA of proliferating cells. A BrdU mouse antibody is then added to detect the incorporated BrdU. Anti-mouse IgG is added and used to recognize the bound detection antibody. A substrate TMB is added to develop color and the magnitude of the absorbance for the developed color is proportional to the quantity of BrdU incorporated into the cells, which is a direct indication of cell proliferation (Leif, R. C. et al. (2004) Cytometry A 58, 45-52).

Figure 4:
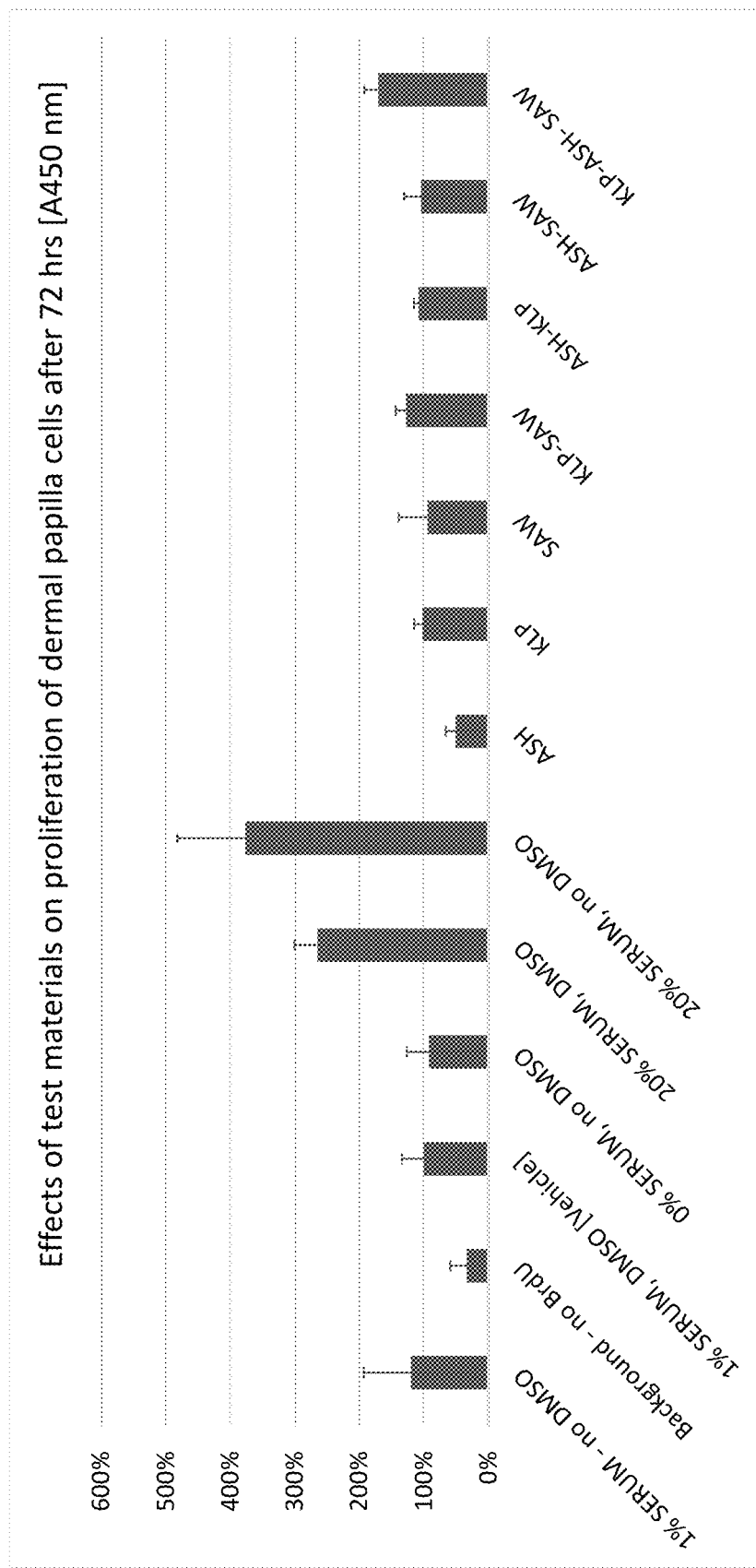
FIG. 4 shows the results of the BrdU Proliferation Assay after 72 hours of treatment with: Ashwaghanda alone, Kelp alone, Saw Palmetto alone, and combinations of Kelp and Saw Palmetto, Ashwaghanda and Kelp, Ashwaghanda and Saw Palmetto, and Kelp, Ashwaghanda and Saw Palmetto, solubilized respectively in 0.8% DMSO.

The BrdU Proliferation Assay was performed after 72 hours of treatment with test materials in the following groups: Ashwaghanda alone, Kelp alone, Saw Palmetto alone, and combinations of Kelp and Saw Palmetto, Ashwaghanda and Kelp, Ashwaghanda and Saw Palmetto, and Kelp, Ashwaghanda and Saw Palmetto, solubilized respectively in 0.8% DMSO. The results are shown in FIG. 4.

Positive controls, containing 20% serum, both showed higher proliferation vs the other control groups containing 1% serum. The negative control, labeled "Background", was not given BrdU to incorporate into the DNA of dividing cells. This Background group showed a very low signal, as expected.

Increased proliferation was also seen when Kelp was added to Saw Palmetto (127%) as compared to Saw Palmetto alone (94%). The results indicate an increase in cell proliferation when adding Kelp to Ashwaghanda (108%), compared to Ashwaghanda alone (51%). Notably, the addition of Kelp to the combination of Ashwaghanda and Saw Palmetto provided 171% increase in cell proliferation as compared to the 104% increase with Ashwaghanda and Saw Palmetto alone. The addition of kelp to the above synergistic ingredient combinations shows increased proliferation of follicular dermal papillae cells.

Example 5—Safety and Efficacy in Promoting Hair Growth in Women with Self-Perceived Thinning Hair The objective of this study was to evaluate the safety and efficacy of daily supplementation with an embodiment of the disclosure comprised of at least 200 mg of curcumin, at least 100 mg of withanolides, and at least 200 mg of bioactive saw palmetto, standardized to contain at least 85% fatty acids and sterols, 10 mg to 1000 mg of tocotrienol and 50 mg to 1000 mg of tocopherols present in a complex comprised of 78% tocotrienols and 22% tocopherols, 225 mcg of iodine, 5 mg of piperine, 500 mg to 2000 mg of hydrolyzed Types I and III collagen having a molecular weight of less than 3000 daltons, and 100 mg to 1000 mg of hyaluronic acid to promote hair growth in women with self-perceived thinning hair.

Methods:

Forty healthy women 21-65 years old with Fitzpatrick skin types I-IV and self-perceived thinning hair were enrolled and randomized in double-blind fashion to receive a composition of the present disclosure (n=26) or placebo (n=14) once daily. The subjects were evaluated at baseline, 3 months and 6 months. A 2 cm$^2$ area of the scalp was selected and marked via triangulation along the juncture of the frontal and lateral hairline. The primary endpoints evaluated were a change in the number of vellus and terminal hairs on phototrichogram analysis at Day 90 and Day 180. Secondary endpoints included blinded investigator physician global hair assessments on hair growth and quality, improvement in terminal hair diameter, hair mass index measurements, and subjects also completed Self-Assessment, Ease of Use and Quality of Life questionnaires at each visit.

Figure 5A:
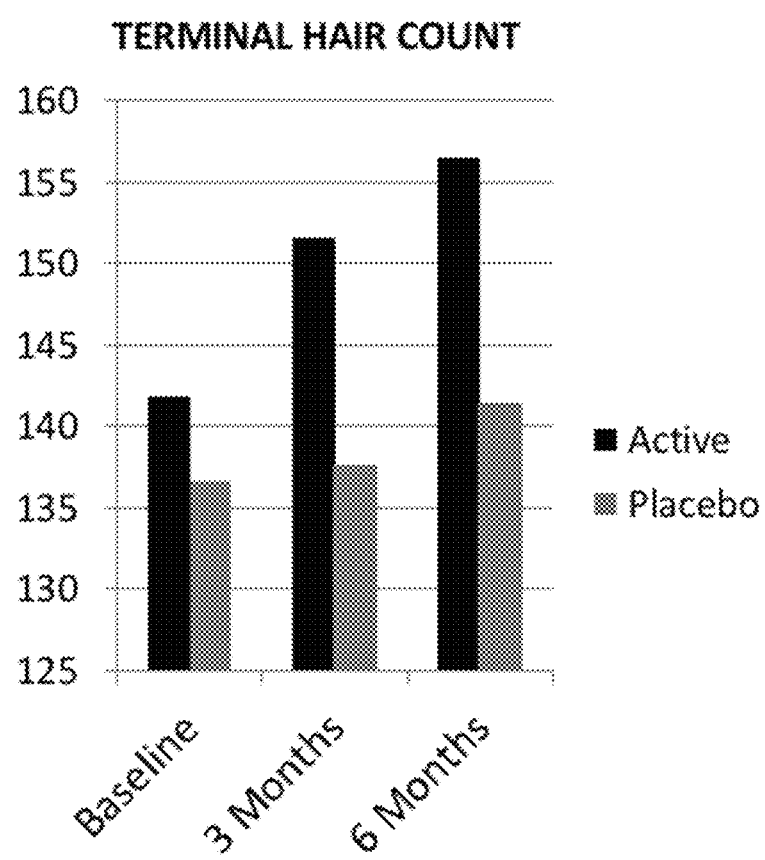
FIG. 5A-FIG. 5D show the results of a safety and efficacy evaluation of a composition of the disclosure in promoting hair growth in women with self-perceived thinning hair.

Results:

As shown in FIG. 5A, there was a significant increase in the number of terminal hairs in the target area at both Day 90 (3 months) and Day 180 (6 months) over baseline in the active group vs placebo ($p<0.0001$). At 6 months, this translated into a 10.3% improvement in terminal hair growth for the active group vs only 3.5% for placebo.

Figure 5B:
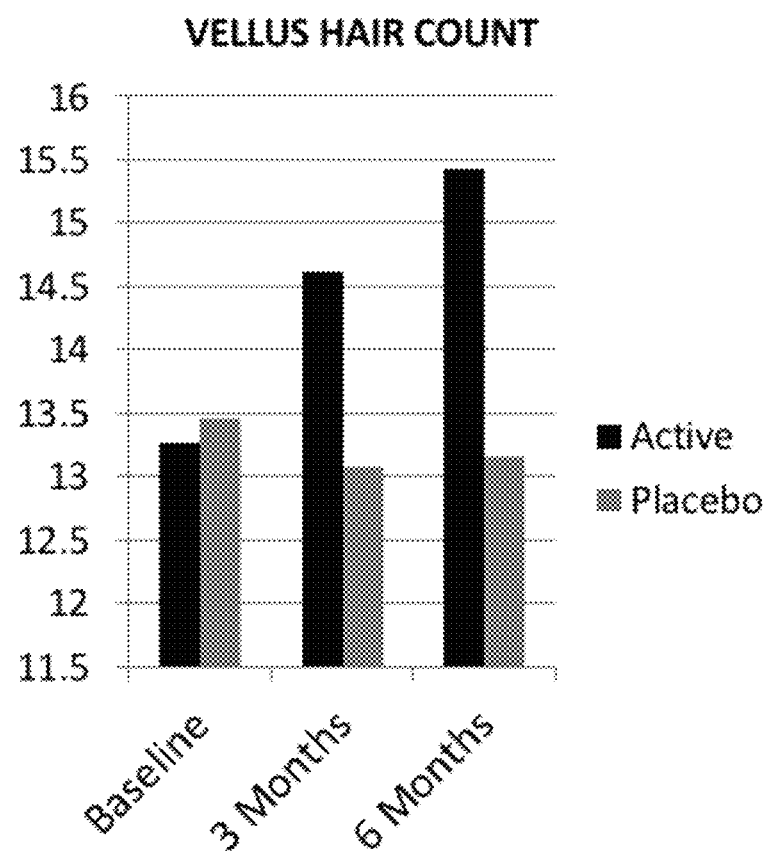

As shown in FIG. 5B, there was a significant increase in the number of vellus hairs in the target area at both Day 90 (3 months) and Day 180 (6 months) over baseline in the active group vs. placebo ($p<0.0001$). At 6 months, this translated into a 16.2% improvement in vellus hair growth for the active group vs. a decrease of 2.3% for placebo.

Figure 5C:
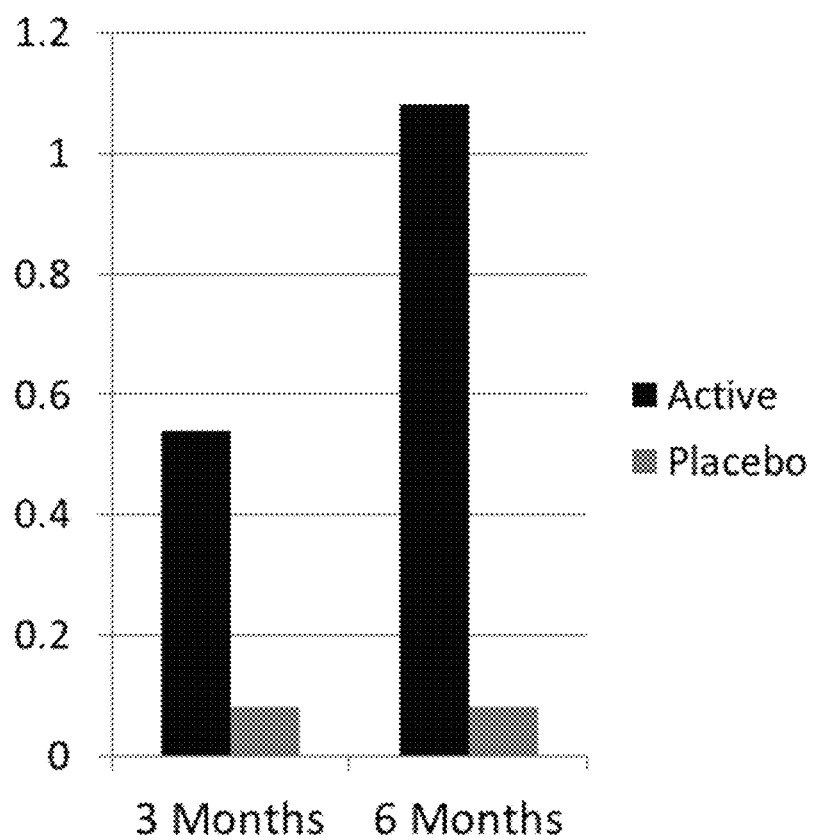

As shown in FIG. 5C, the active group had statistically significant improvement versus placebo in hair growth at 6 months. The mean hair growth global improvement scale scores were 1.08 (1.1) for the active group and 0.08 (0.76) for the placebo group ($p<0.016$).

Figure 5D:
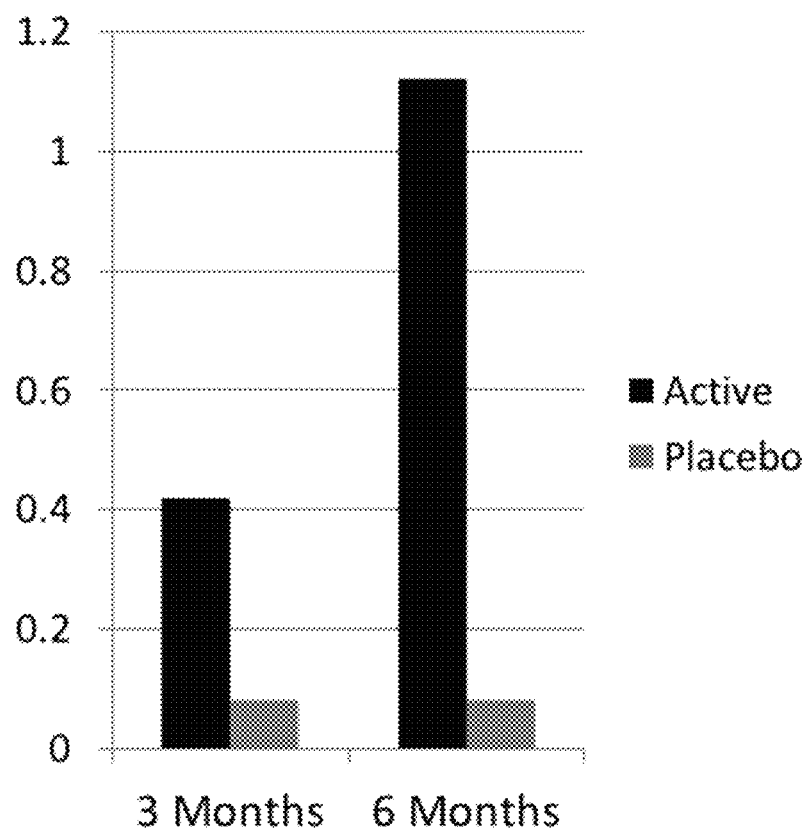

As shown in FIG. 5D, there was significant improvement in the active group compared to the placebo group at both 3 and 6 months. At 6 months the mean hair quality global improvement scale scores were 1.12 (0.87) for the active group and 0.08 (0.76) for the placebo group ($p<0,05$). Hair quality was rated based on hair brittleness, dryness, texture, shine, scalp coverage and overall appearance.

Images from an active subject at baseline, 3 months and 6 months are shown in FIG. 6A-FIG. 6F.

Table 1 shows the results of a self-assessment questionnaire after taking active composition for 6 months.

TABLE 1

| % OF SUBJECTS IMPROVED | QUALITY |
|---|---|
| 80.8%* | Overall hair growth |
| 73.1%* | Overall hair volume |
| 80.8%* | Thickness of hair body |
| 23.1%* | Hair color |
| 76.9%* | Amount of noticeable new hair |
| 73.1%* | Hair growth rate |
| 15.4%* | Stress level |
| 15.4%* | Anxiety level |
| 19.2%* | Overall well-being |
| 23.1%* | Skin smoothness |
| 26.9%* | Overall skin health |

Safety Assessment:

There were no reported adverse events or side effects. Subjects found it to be well tolerated and easily incorporated into their daily routines.

Conclusion:

The results of this study indicate that daily supplementation with the active composition of the disclosure resulted in increased hair growth in women with self-perceived thinning hair. A vast majority of treated subjects also reported positive results in key hair quality and wellness attributes. The study composition provides a safe and effective therapeutic option for improving hair growth in women with thinning hair.

ADVANTAGES OF THE INVENTION

The compositions of the disclosure thus produced significant and visible benefits in mitigating hair loss and promoted new hair growth.

While the present disclosure has been described in terms of exemplary aspects, those skilled in the art will recognize that the present disclosure can be practiced with modifications in the spirit and scope of the appended claims. These examples and embodiments given above are merely illustrative and are not meant to be an exhaustive list of all possible designs, aspects, applications or modifications of the present disclosure.

What is claimed is:

1. A method of improving hair loss caused by androgenetic alopecia, alopecia areata, alopecia mucinosa, telogen effluvium, chronic inflammation, extreme and/or chronic stress, diabetes, cellulitis, hair treatments, hereditary disorders, hormonal changes, hyperthyroidism, hypothyroidism, malnutrition, lupus, medication side effects, radiation, aging and trichotillomania, comprising administering to a subject in need thereof an effective amount of a composition comprising:
about 100 mg to 1000 mg of an extract of *Curcuma longa*,
from about 100 mg to 1000 mg of an extract of the roots and leaves of *Withania somnifera*,
at least about 200 mg of saw palmetto extract,
from about 225 mcg to 300 mcg of iodine, and
a pharmaceutically acceptable encapsulating material,
for a time sufficient to improve hair loss.

2. The method of claim 1, wherein said iodine is provided by kelp.

3. The method of claim 1, wherein the composition further comprises from about 100 mg to about 1000 mg of tocotrienols and tocopherols.

4. The method of claim 1, wherein the composition further comprises low molecular weight collagen and hyaluronic acid.

5. The method of claim 4, wherein said collagen is Type I and Type III collagen and has a molecular weight of less than 5000 daltons.

6. The method of claim 4, wherein said collagen is present in an amount from about 500 mg to about 2000 mg, and said hyaluronic acid is present in an amount from about 100 mg to about 1000 mg.

7. The method of claim 1, wherein the composition further comprises at least about 5 mg of piperine.

8. The method of claim 1, wherein the composition further comprises one or more compounds selected from the group consisting of green tea extract, L-methionine, L-cysteine hydrochloride, resveratrol, capsaicin, biotin, selenium, Vitamin D, Vitamin A, Vitamin C, choline, calcium and copper.

9. A method of improving hair loss caused by androgenetic alopecia, alopecia areata, alopecia mucinosa, telogen effluvium, chronic inflammation, extreme and/or chronic stress, diabetes, cellulitis, hair treatments, hereditary disorders, hormonal changes, hyperthyroidism, hypothyroidism, malnutrition, lupus, medication side effects, radiation, aging and trichotillomania, comprising administering to a subject in need thereof an effective amount of a composition comprising:

at least about 200 mg of curcumin,
   at least about 100 mg of withanolides,
   at least about 200 mg of saw palmetto extract,
   at least about 100 mg of tocotrienols and tocopherols comprising a complex of about 78% tocotrienols and about 22% tocopherols,
   at least about 225 mcg of iodine,
   at least about 1000 mg of Type I and III collagen having a molecular weight of less than about 3000 Daltons,
   at least about 100 mg of hyaluronic acid, and
   a pharmaceutically acceptable encapsulating material,
for a time sufficient to improve hair loss.

\* \* \* \* \*